United States Patent
Loescher

(10) Patent No.: US 8,469,024 B2
(45) Date of Patent: Jun. 25, 2013

(54) TRACHEOSTOMY TUBE ASSEMBLY AND PAD

(75) Inventor: Thomas C. Loescher, Rancho Santa Fe, CA (US)

(73) Assignee: A Plus Medical, Carlsbad, CA (US)

( * ) Notice: Subject to any disclaimer, the term of this patent is extended or adjusted under 35 U.S.C. 154(b) by 1219 days.

(21) Appl. No.: 12/268,949

(22) Filed: Nov. 11, 2008

(65) Prior Publication Data

US 2009/0126740 A1    May 21, 2009

Related U.S. Application Data

(60) Provisional application No. 60/988,314, filed on Nov. 15, 2007.

(51) Int. Cl.
*A61M 16/00*    (2006.01)
(52) U.S. Cl.
USPC ................................ 128/201.27; 128/201.24
(58) Field of Classification Search
USPC .................... 5/636, 638, 637, 652.1; 482/49, 482/141; 401/282, 286
See application file for complete search history.

(56) References Cited

U.S. PATENT DOCUMENTS

| | | | |
|---|---|---|---|
| 3,422,817 A | | 1/1969 | Mishkin et al. |
| 4,617,691 A | * | 10/1986 | Monti et al. ..................... 5/640 |
| 5,058,579 A | | 10/1991 | Terry et al. |
| 5,471,980 A | | 12/1995 | Varner |
| D385,741 S | * | 11/1997 | Lebenbaum .................. D6/601 |
| 5,918,599 A | | 7/1999 | Shesol |
| 6,105,577 A | | 8/2000 | Varner |
| 6,793,434 B1 | * | 9/2004 | Olson ........................... 401/286 |

\* cited by examiner

*Primary Examiner* — Jerome W Donnelly
(74) *Attorney, Agent, or Firm* — Knobbe Martens Olson & Bear, LLP

(57) ABSTRACT

A tracheostomy tube assembly comprising a tracheostomy tube and an elongated neck plate secured to said tube having an upper edge, a lower edge and holes at opposite ends thereof, is characterized by a soft, flexible gel-like polymer pad having a center port surrounding the tracheostomy tube and releasably secured on the patient side of the neck plate and extending to or beyond the upper and lower neck plate edges and inside the holes. The pad has a smooth, substantially flat, planar first surface for resting against the patient side of the neck plate and a smooth, soft, transversely concave second surface for resting against a patient's neck, whereby the pad has a thicker cross-section at its opposite side edges and ends, and a thinner cross-section along a center portion extending between the upper and lower pad edges and ends.

24 Claims, 5 Drawing Sheets

TRACHEOSTOMY TUBE ASSEMBLY AND PAD

CROSS-REFERENCE TO RELATED APPLICATIONS

This application claims priority to U.S. Provisional Application No. 60/988,314 filed on Nov. 15, 2007, the contents of which are hereby incorporated by reference in their entirety.

BACKGROUND OF THE INVENTION

A tracheostomy procedure is performed to create an opening or stoma through the neck of a patient into the trachea or windpipe. The tracheotomy is used to bypass an obstructed airway, clean and remove secretion and/or to more easily deliver oxygen to the patient's lungs. A tracheostomy tube is inserted through the stoma to keep it open as well as to provide a device which may be connected to oxygen delivery apparatus or systems.

The components of a typical tracheostomy tube are well known to those skilled in the art and include a machine end which projects outwardly from the neck of the patient, and which may be configured to mate with the breathing system of an anesthetic machine, a ventilator or other oxygen delivery apparatus. Other components include an outer tube which is inserted into the trachea and is in contact with patient tissue, and an inner tube which fits closely to the inside contours of the outer tube. An inflatable balloon is permanently attached around the tracheostomy tube (outer tube) near the patient end within the trachea. The inflatable balloon, when inflated, provides a seal between the tube and the trachea. The cuff is inflated through an inflating tube secured along the outer tube with a pilot balloon fitted to the distal end of the inflating tube, opposite the end communicating with the cuff. A neck plate is secured to the tube adjacent to the machine end, and is provided with holes at each end for attaching straps or strips to encircle the patient's neck in order to hold and maintain the tracheostomy tube on the patient. Such components as well as other descriptions are well known to those skilled in the art and are described in further detail in the International Organization for Standardization document ISO5366.

A tracheostomy dressing comprising an absorbent gauze pad is typically secured around the tracheostomy tube between the neck plate and the patient's neck in order to absorb and collect trachea secretions. Examples of such pads or dressings are described in U.S. Pat. Nos. 3,422,817, 5,058,579 and 5,918,599. However, the problem with such gauze absorbent pads is that the material often causes inflammation of the patient's skin at and adjacent to the stoma. Thus, not only does the gauze pad need to be changed, but continued irritation of the inflamed skin requires medical treatment to reduce the inflammation and prevent infection as well as to avoid further patient discomfort.

SUMMARY OF THE INVENTION

Embodiments of the invention are directed to a soft, very flexible, plastic pad surrounding the tracheostomy tube between the neck plate and the patient. The pad has a substantially planar flat surface for lying against and engaging the neck plate, and an opposite concave surface for engaging and resting against the patient's neck. The pad described herein may also be used for protecting stomas at other body locations where a fluid-directing tube enters the patient's body. Further description and advantages of the pad and its use will be described in the detailed description.

DETAILED DESCRIPTION

Figure 1:
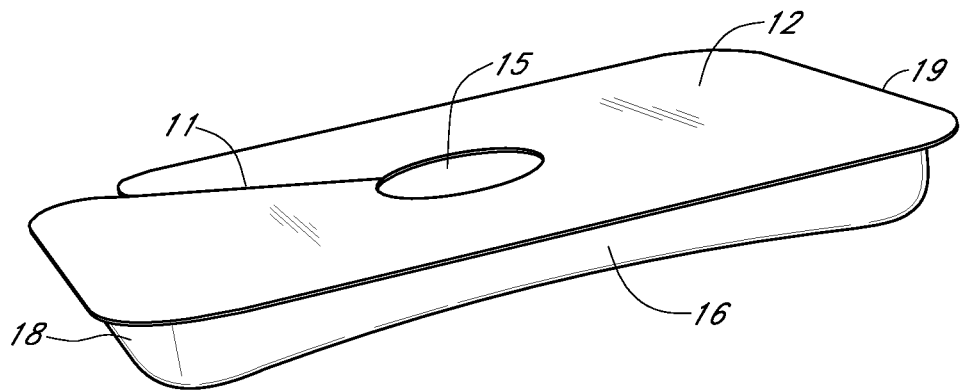
FIG. 1 is an isometric top view of the pad.
Figure 2:
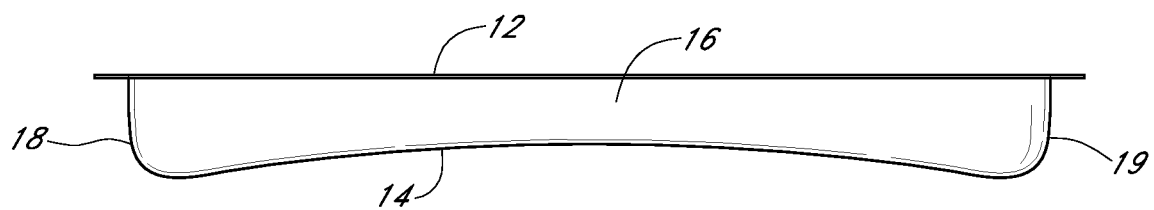
FIG. 2 is a side view of the pad.
Figure 3:
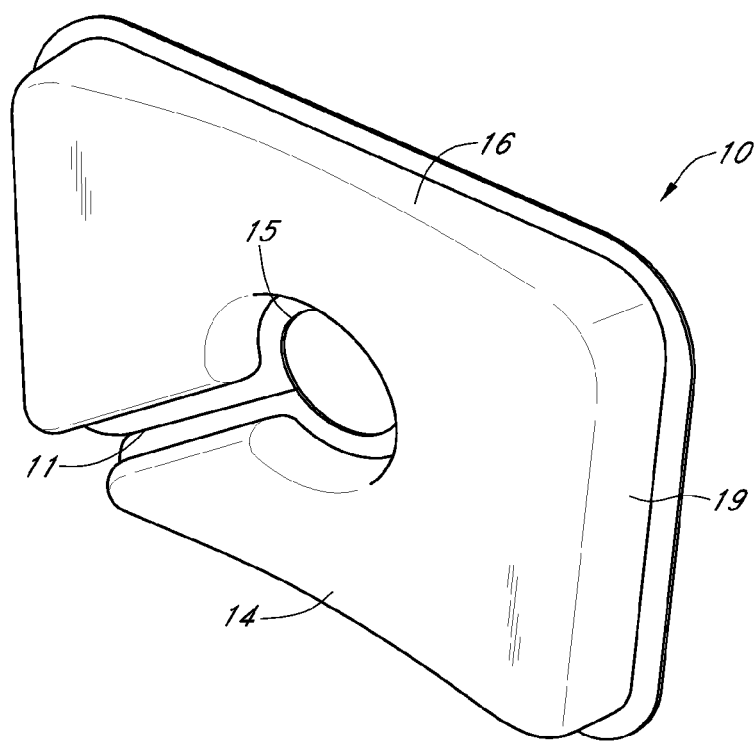
FIG. 3 is an isometric bottom view of the pad.
Figure 4:
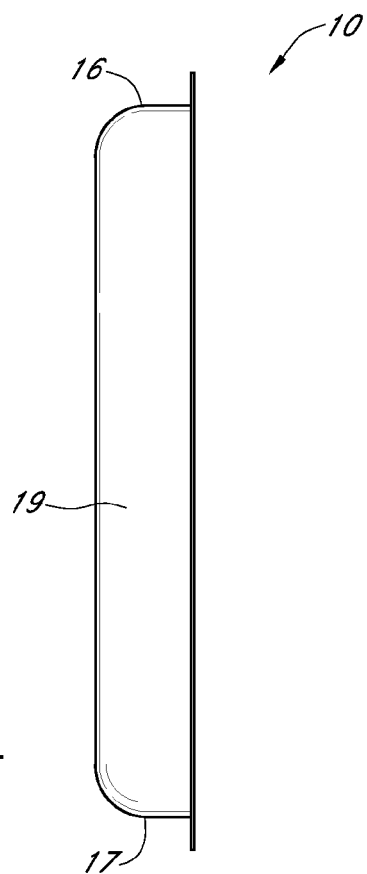
FIG. 4 is an end view of the pad.
Figure 5:
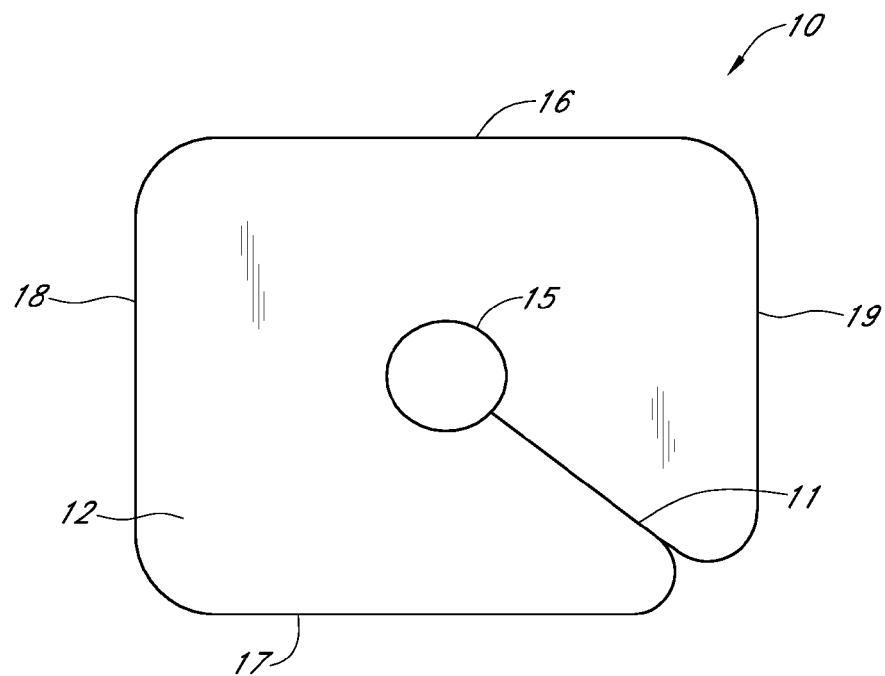
FIG. 5 is a top plan view of the pad.

Observing FIGS. 1-5, the tracheostomy pad embodiment shown is generally rectangular with a top surface 12 and an opposite concave surface 14. The corners at the intersection of the upper edge 16 and lower edge 17 with side edges 18 and 19 may be rounded as shown. The surface 12 may be flat, planar and smooth as shown in the drawings and for resting against the patient side of the neck plate of a tracheostomy tube assembly. The shape of the pad may be rectangular, square, round, oblong, oval or other shape so long as the top surface is flat and planar and the bottom surface 14 is generally uniformly concave and smooth from side to side. It may be desirable to configure the shape of the pad to reflect or generally follow the outline or other shape of a neck plate or other tube-supporting plate. For example, the pad may be wing-shaped to follow the contour of a pediatric or neonatal tracheostomy plate.

The concave bottom surface 14 is generally uniform and smooth between the side edges 18 and 19 and is formed along the entire face or surface 14 between the upper and lower edges 16 and 17. This feature is best observed in FIGS. 1 and 2. In such a configuration, the pad is thickest at the opposite side edges 18 and 19 and the thinnest in the center of the pad. If the pad is round, oval or oblong, the pad (cross-section) is thickest at or adjacent to the opposite side edges or ends and thinnest (cross-section) at or adjacent to the center of the pad, between the upper and lower pad edges or ends.

In one embodiment, the ratio of the center cross-sectional thickness:side edge cross-sectional thickness is between about 1:3 and about 1:1.1, respectively. In another embodiment, the ratio of the thickness of the pad at the center:side edges is between about 1:3 and about 1:1.3, respectively. In other embodiments, the ratios are between 1:3 and 1:1.5. Specific cross-sectional thicknesses of the pad along the side edge surface may be between about 3 mm and about 15 mm, and the center cross-sectional dimension thickness is between about 1.5 mm and about 12 mm. Again, the concave surface from side edge to side edge may be smooth and uniformly concave to the center of the pad. By way of specific example, center:side edge thickness dimensions may be 1.5 mm:3.0 mm, 3.0 mm:5.0 mm, 7.0 mm:9.10 mm, and 10.0 mm:12.0 mm.

An orifice or port 15 through the pad is located substantially at the center of the pad. The dimension of the port may be oversized relative to the tracheostomy tube to prevent the pad from engaging the outer surface of the tracheostomy tube and allows movement of the pad without interfering with the tube.

In one embodiment, the pad is made of a very soft and flexible polyurethane or silicone rubber. A specific example of one material is a polyurethane having a shore A durometer hardness of between about 15 and about 40. Another pad composition comprises a soft silicone gel encased in a thin, flexible, soft polyurethane cover, layer or skin. Such a composition and methods of manufacture are known to those skilled in the art. The flexibility of such materials is such that the pad can be readily installed on the tracheostomy tube with the surface 12 resting against the neck plate of the tracheostomy tube assembly. Moreover, because the material may be pliant and flexible, the surface 12 can thereby conform to the neck plate surface shape, whether flat, curved or other shape when the pad is installed on the assembly. The material may be treated with an anti-microbial material such as silver nitrate or with a composition capable of releasing antiseptic or other composition to resist and prevent infection of the patient's neck skin against which the pad rests.

In another embodiment, the pad is provided with a slit, channel or groove extending through the thickness of the pad from an outer edge or corner to the center port. The outer edge may be a side edge or upper or lower end. In the embodiment shown in FIGS. 1, 3, and 5, slit 11 extends from a corner of the pad to center port 15. The slit may be a straight, narrow cut through the thickness of the pad, or it may be a broader channel. This feature allows the pad to be opened or separated along the slit so that a physician, therapist, nurse or other operator can easily install or remove the pad from the tube, without removing the tube and without traumatizing the patient. However, in another embodiment the pad is not provided with such a slit, and the pad material is sufficiently flexible and resilient so that it may be installed on the tracheostomy tube at the patient end and stretched over the inflatable cuff and urged to its aforesaid position.

Figure 6:
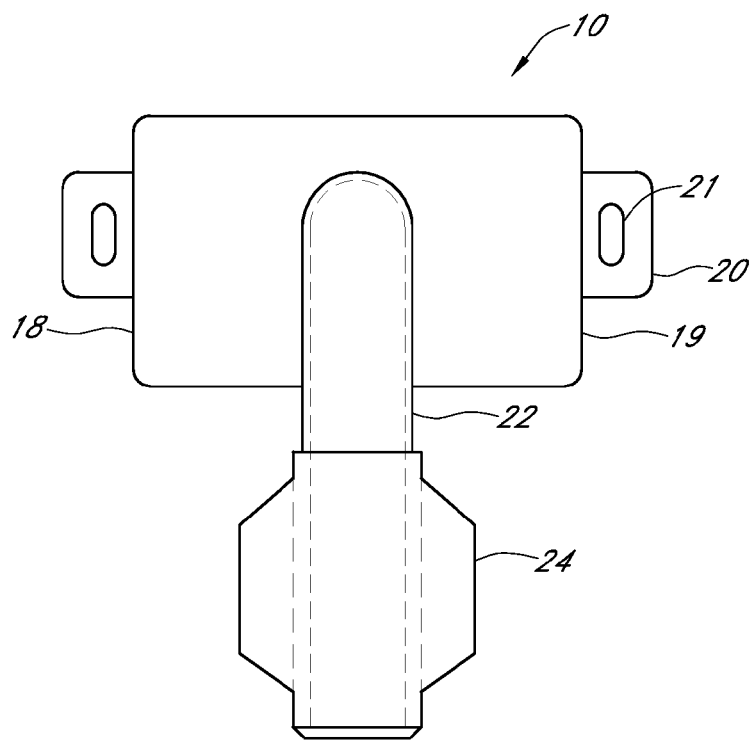
FIGS. 6-8 are back, top and side views, respectively, of a tracheostomy tube assembly with the tracheostomy pad positioned on the tube.
Figure 7:
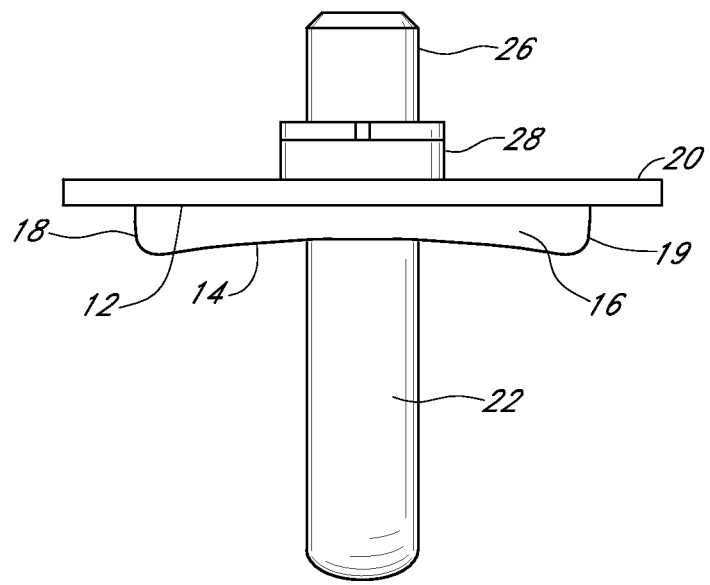
Figure 8:
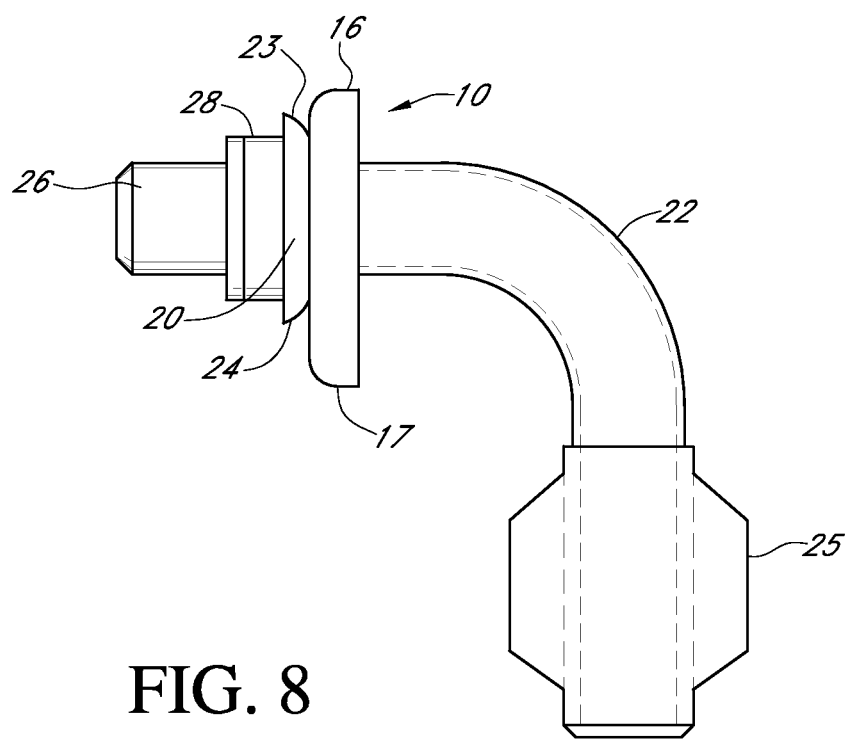

The tracheostomy tube assembly with the tracheostomy pad of the invention installed is illustrated in FIGS. 6-8. The tracheostomy tube assembly includes an outer tube 22 with an inflatable cuff 25 adjacent to the patient end of the tube. A neck plate 20 is secured to the tracheostomy tube 22 against or secured to neck plate collar 20 which is integral with or firmly attached to tube 22. The tracheostomy pad 10 is positioned along tracheostomy tube 22 with its flat, planar surface 12 resting against the neck plate 20 and the concave surface 14 positioned on the patient side of the assembly. Although the neck plate shown in the drawings is flat, it may instead be curved or arch shaped. Because the pad described herein is soft, pliant and flexible, it will conform to the adjacent neck plate surface against which it is urged in the assembly and positioned on the patient.

The size of the pad may be such that its upper edge 16 extends beyond the upper edge 23 of neck plate 20 and the lower edge 17 of the pad extends beyond the lower edge 24 of the neck plate. However, the pad may also be smaller than the neck plate. The horizontal dimension of the pad may be such that the side edges 18 and 19 do not cover up neck plate holes 21 to avoid interference with any ties, ribbons or other components for securing the tube assembly on a patient. Moreover, the pad may be sized and shaped to fit or cover any tube-holding plate shape or size. The tracheostomy tube assembly shown in FIGS. 7 and 8 also includes the male connector or machine end of an inner tube as previously explained in the background portion of the specification.

Figure 9:
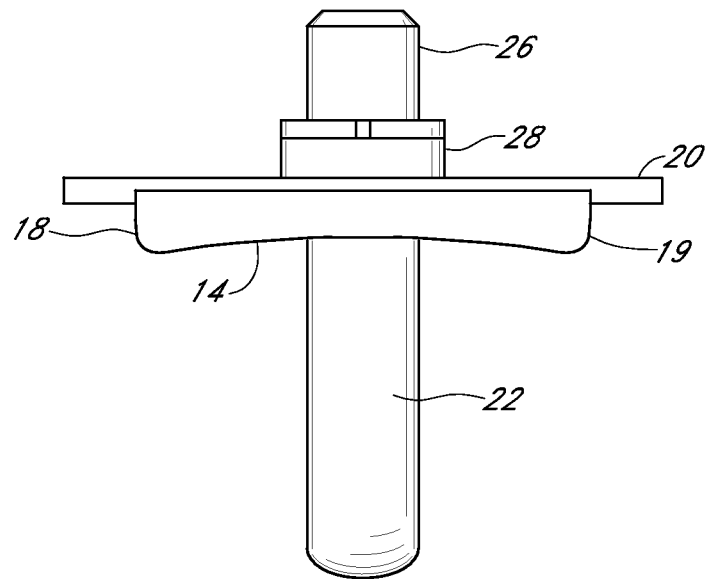
FIGS. 9 and 10 are top and side views, respectively, of a tracheostomy tube assembly showing another tracheostomy pad embodiment.
Figure 10:
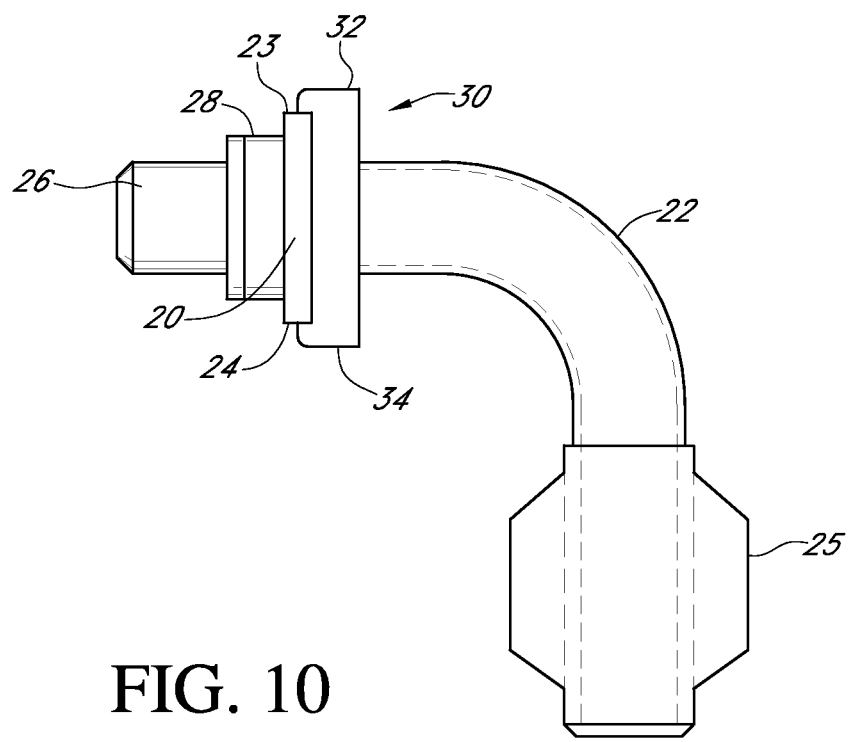

In FIGS. 9 and 10, another pad embodiment is illustrated. Pad 26 shown is oversized relative to the height of neck plate 20 such that the upper and lower edges 32 and 34 of the pad extend beyond and overlie the upper and lower edges, respectively, of the neck plate. As illustrated, such feature creates a cavity or channel along the pad between side edges 18, 19 for receiving the neck plate.

With the tube assembly secured on a patient, the soft, flexible pad's concave surface prevents irritation of the patient's skin and avoids the previously described disadvantages of gauze absorbent pads or other materials. As previously stated, the use of the pad described herein is not limited to a tracheostomy, and may be effectively used at any site where it is desirable to cushion and prevent stoma wound irritation by a tube-holding flange and install the pad without removing the tube.

What is claimed is:

1. A pad configured to be secured to a fluid tube assembly on the patient side of a tube-holding plate thereof, said pad comprising:
   a flexible substantially flat planar surface configured to rest against said tube-holding plate;
   a transversely concave surface opposite said planar surface;
   a pair of side edge surfaces disposed along two opposite sides of the pad, and wherein the cross-sectional thickness of said pad between said planar surface and said concave surface is greater along said side edge surfaces and diminishes from both side edge surfaces to the center of said pad; and
   a circular port located substantially at the center of said pad.

2. A pad of claim 1 wherein the shape of said pad is substantially rectangular.

3. A pad of claim 1 wherein the shape of said pad is circular, oval or oblong.

4. A pad of claim 1 wherein the cross-sectional thickness of said pad along said side edge surfaces is between about 3 mm and about 15 mm and wherein the thinnest center cross-sectional dimension is between about 1.5 mm and about 12 mm.

5. A pad of claim 2 wherein the cross-sectional thickness of said pad along said side edge surfaces is between about 3 mm and about 15 mm and wherein the thinnest center cross-sectional dimension is between about 1.5 mm and about 12 mm.

6. A pad of claim 1 comprising polyurethane or silicone rubber.

7. A pad of claim 4 comprising polyurethane or silicone rubber.

8. A pad of claim 1 comprising a silicone gel coated with a thin layer of polyurethane.

9. A pad of claim 1 wherein the ratio of the cross-section thickness of said pad at the center:side edge is between about 1:3 to about 1:1.1, respectively.

10. A pad of claim 1 having a slit or channel therethrough extending from an outer edge surface or corner to the center port.

11. A pad of claim 5 having a slit or channel therethrough extending from an outer edge surface or corner to the center port.

12. A pad of claim 9 having a slit or channel therethrough extending from an outer edge surface or corner to the center port.

13. A pad of claim 5 comprising a silicone gel coated with a thin layer of polyurethane.

14. A pad of claim 6 comprising a silicone gel coated with a thin layer of polyurethane.

15. A pad of claim 9 comprising a silicone gel coated with a thin layer of polyurethane.

16. A tracheostomy pad configured to be secured to a neck plate of a tracheostomy tube, said pad comprising:
- a flexible substantially flat planar surface configured to mate with the neck plate of a tracheostomy tube;
- a transversely concave surface opposite said flat planar surface,
- a pair of side edge surfaces disposed along two opposite sides of the pad, wherein the cross-sectional thickness of said pad between said planar surface and said concave surface is greater along said side edge surfaces and diminishes from both side edge surfaces to the center of said pad;
- a circular port located substantially at the center of said pad; and
- a slit extending through the pad from the circular port to an outer edge surface.

17. A tracheostomy pad of claim 16, wherein the slit extends from the circular port to a corner of the pad.

18. A tracheostomy pad of claim 16, wherein the pad comprises a silicone gel interior coated with a layer of polyurethane.

19. A tracheostomy pad of claim 16, wherein the ratio of the cross-sectional thickness of the pad at the center to the cross-sectional thickness at a side edge is between about 1 to 3 to about 1 to 1.1, respectively.

20. A tracheostomy pad of claim 16, wherein the cross-sectional thickness of said pad along said side edge surfaces is between about 3 mm and about 15 mm.

21. A tracheostomy pad of claim 16, wherein the thinnest center cross-sectional dimension is between about 1.5 mm and about 12 mm.

22. A tracheostomy pad of claim 16, wherein the shape of said pad is substantially rectangular.

23. A tracheostomy pad of claim 16, wherein the shape of said pad is circular, oval or oblong.

24. A tracheostomy pad of claim 16, wherein the pad comprises an antimicrobial agent.

* * * * *